United States Patent [19]

Engel

[11] Patent Number: 4,554,924

[45] Date of Patent: Nov. 26, 1985

[54] CONDUCTIVE ADHESIVE AND BIOMEDICAL ELECTRODE

[75] Inventor: Michael R. Engel, White Bear Lake, Minn.

[73] Assignee: Minnesota Mining and Manufacturing Company, St. Paul, Minn.

[21] Appl. No.: 299,570

[22] Filed: Sep. 4, 1981

Related U.S. Application Data

[63] Continuation-in-part of Ser. No. 114,565, Jan. 23, 1980, abandoned.

[51] Int. Cl.[4] ............................................. A61B 5/04
[52] U.S. Cl. .................................. 128/640; 128/798; 252/500
[58] Field of Search ........................... 128/639–641, 128/644, 798, 802, 803, 303.13; 252/500

[56] References Cited

U.S. PATENT DOCUMENTS

| | | | |
|---|---|---|---|
| 4,066,078 | 1/1978 | Berg | 128/2.06 E |
| 4,220,159 | 9/1980 | Francis et al. | 128/639 |
| 4,237,886 | 12/1980 | Sokurada et al. | 128/798 X |
| 4,248,247 | 2/1981 | Ware et al. | 128/802 X |
| 4,274,420 | 6/1981 | Hymes | 128/641 |
| 4,352,359 | 10/1982 | Larimore et al. | 128/640 |
| 4,391,278 | 7/1983 | Cahalen et al. | 128/640 |

OTHER PUBLICATIONS

U.S. patent application Ser. No. 155,191 filed Jun. 2, 1980, Larimore et al.

*Primary Examiner*—Lee S. Cohen
*Attorney, Agent, or Firm*—Donald M. Sell; James A. Smith; Carolyn A. Bates

[57] ABSTRACT

A disposable biomedical electrode is disclosed wherein the electrically-conductive material between the electrode plate and the skin comprises a swellable, conformable, cohesive, hydrophilic, electrically-conductive adhesive formed by an improved solventless process. The adhesive precursor comprises a polyhydric alcohol, a non-ionic unsaturated free radically polymerizable material, a free radical initiator, a crosslinking agent and an ionizable salt. The adhesive precursor is polymerized after coating onto the electrode plate or releasable transfer sheet, preferably by exposure to ultraviolet radiation.

12 Claims, 4 Drawing Figures

U.S. Patent  Nov. 26, 1985  4,554,924
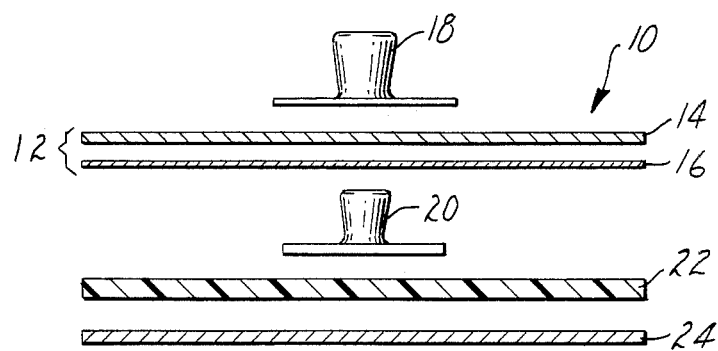
FIG. 1
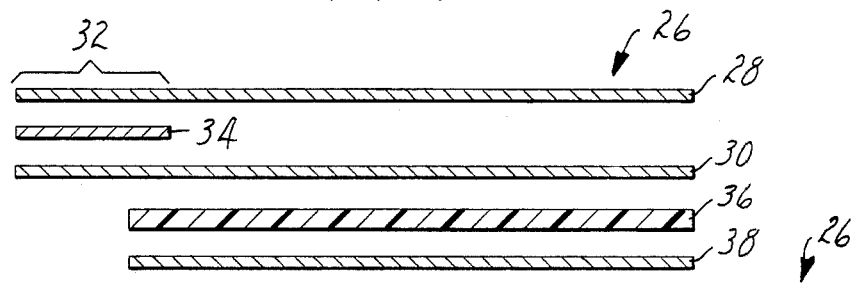
FIG. 3
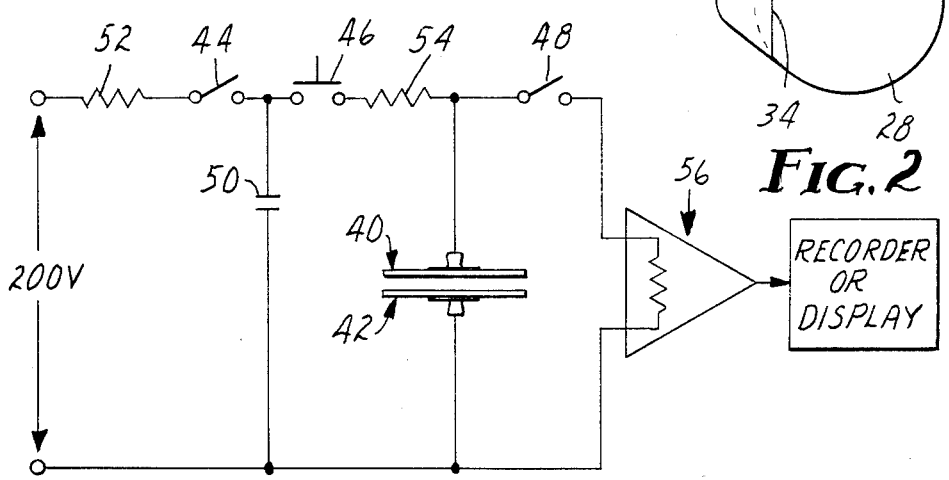
FIG. 2
FIG. 4

CONDUCTIVE ADHESIVE AND BIOMEDICAL ELECTRODE

RELATED APPLICATIONS

This application is a continuation-in-part of my copending application, Ser. No. 114,565, filed Jan. 23, 1980, now abandoned.

FIELD OF THE INVENTION

This invention relates to the field of conductive adhesives, particularly those used in biomedical electrodes to establish an electrical connection between the skin of the human anatomy and an electromedical apparatus, such as a high impedance electromyograph, electrocardiograph, electrical neurostimulator for pain relief, and the like. More particularly, it relates to conductive adhesives for use in so-called "dry" bioelectrodes which do not require the use of messy creams or gels to enhance conductivity between the skin and the electrode plate.

BACKGROUND ART

My copending application Serial No. 114,565 disclosed a conductive adhesive for biomedical electrode applications made by an improved solventless process. The adhesive is synthetic, dermally-nonirritating, conformable, cohesive, ionic and hydrophillic. The process by which the electrode is made involves the steps of: (1) forming an adhesive precursor comprising (a) a water-soluble polyhydric alcohol which is liquid at room temperature, (b) an ionic unsaturated free-radically polymerizable material which is soluble in the polydric alcohol, (c) a free radical initiator which is soluble in the polyhydric alcohol, and (d) a multi-functional unsaturated free radically polymerizable cross-linking agent; (2) coating the adhesive precursor on one side of an electrode plate (conductive sensing element); and (3) polymerizing the coated precursor in situ.

In the preferred embodiment of the conductive adhesive of the aforementioned disclosure, the ionic monomer is acrylic acid neutralized with an inorganic base such as potassium hydroxide.

The conductive adhesives of my previous disclosure are especially useful in electrosurgical grounding plate electrodes. They offer significant advantages over prior art conductive adhesives such as those described by Berg in U.S. Pat. No. 4,066,078. Berg discloses two classes of conductive adhesives plasticized with a polyhydric alcohol, viz., (1) polymers or copolymers derived from the polymerization of an ester of an olefinically unsaturated carboxylic ester and an alcohol having a quarternary ammonium group, and (2) sulfated cellulose esters. The processes by which these adhesives are formed into electrodes are much more tedious and expensive than those described in my previous disclosure and do not result in as good overall adhesive properties. The conductive adhesives of my previous disclosure are also an improvement over those specifically described in the copending application of Larimore et al, Ser. No. 155,191, filed June 2, 1980, now U.S. Pat. No. 4,352,359. The Larimore conductive adhesives may be formed from similiar ionic monomers, but a more expensive process is used and no crosslinked polymers are disclosed. Crosslinking allows for higher amounts of polyhydric alcohol without reducing viscosity below acceptable levels. A higher polyhydric alcohol level enhances hydrophilicity, thereby improving electrical conductivity.

Although the conductive adhesives of my previous disclosure provide significant improvements over the prior art, particularly when used in grounding plate electrodes, one problem has been encountered with their use in ECG electrodes. Electrodes utilizing my prior conductive adhesives do not recover satisfactorily following a defibrillation overload when used in disposable ECG electroces. Their polarization potential is too high to meet standards proposed by the Association for the Advancement of Medical Instrumentation (AAMI).

I have now discovered that by the addition of ionic salts, preferably those containing a halide ion, to the electrically-conductive adhesives of my prior disclosure, I am able to produce non-polarizing electrodes. Since the added salts provide the conductivity needed for good electrical performance, inclusion of an ionic monomer in the adhesive precursor is no longer necessary.

BRIEF SUMMARY OF THE INVENTION

According to the present invention, there is provided an essentially dry disposable biomedical electrode comprising an electrode plate or sensing element having a top surface and a bottom, skin-directed surface. The electrode plate has a means for electrical connection to a lead wire of an electro-medical device. The bottom surface of the electrode plate is coated with a swellable, non-water-soluble, conformable, cohesive, dermally-nonirritating, hydrophilic conductive material for enhancing the electrical connection with the skin. The conductive material is formed from an essentially solventless process in situ on the electrode plate or a transfer sheet. The process involves first forming an adhesive precursor comprising (1) a water-soluble polyhydric alcohol which is a liquid at about 20° C.; (2) at least one non-ionic unsaturated free radically polymerizable material soluble in said polyhydric alcohol; (3) a free radical initiator soluble in said polyhydric alcohol; (4) a crosslinking agent of a multifunctional unsaturated free radically polymerizable material soluble in said polyhydric alcohol; and (5) an ionizable salt in an amount effective to render said adhesive product electrically conductive.

The non-ionic polymerizable material may comprise one non-ionic monomer or a mixture of non-ionic monomers. It is also contemplated that ionic polymerizable materials which are soluble in the polyhydric alcohol may be included in the precursor without departing from the spirit of the invention.

The adhesive precursor is coated directly onto one surface of the electrode plate or onto a releasable transfer surface. The precursor is polymerized in situ, preferably by ultraviolet radiation to form an adhesive layer which is a continuous covalently-bonded network throughout. The cured conductive layer is then ready for use. If polymerization occurs on a transfer surface, the adhesive layer is stripped from the transfer surface and applied to the electrode plate. An ECG electrode containing the conductive adhesive of the invention should exhibit a "Polarization Potential" (as hereinafter defined) which does not exceed 100 millivolts.

The term "solventless" is used herein to mean that there are substantially no materials present in the adhesive precursor which are not present in the final composition of the electrically conductive adhesive. Stated another way, when the polymerization of the precursor is complete, and the adhesive is ready for use, at least 99% of the starting materials are still present.

The term "hydrophilic" is used herein to mean the conductive adhesive will absorb some water.

The term "conformable" as used herein refers generally to the compliance of the conductive material. It must be sufficiently compliant to conform to the surface of the skin beneath the electrode plate to provide a high surface area of contact between the skin and the electrode plate.

The term "cohesive" refers to the internal integrity of the conductive material. Generally, the conductive material is film-forming and must be more cohesive than adhesive to the skin so that, when the electrode is removed from the skin, the conductive layer remains intact and does not leave an objectionable residue.

The term "swellable" refers to the imbibing of solvents by the polymer matrix with a concomitant increase in the volume of the polymer matrix.

The term "dermally non-irritating" means that the conductive adhesive can be used safely on mammalian skin without causing an unacceptable amount of irritation or other toxic side effects.

DETAILED DESCRIPTION

The electrically conductive material is derived from the essentially solventless process of polymerizing the adhesive precursor of which one component is the water-soluble polyhydric alcohol. The term "polyhydric alcohol" as used herein refers to a compound or polymer having more than one hydroxyl group. The polyhydric alcohol is water soluble and a liquid at room temperature, e.g., approximately 20° C. The polyhydric alcohol is present in the precursor in amounts of from 10 to 90 parts per weight of the precursor, with 50 to about 70 being preferred. Examples of useful polyhydric alcohols are propylene glycol; 1,2,4 butane triol; polyethyleneoxide (e.g., "Carbowax" 400); and glycerol, with the latter being preferred. One skilled in the art will recognize that polyhydric alcohols which are not normally liquid at room temperature, may be mixed with those that are liquid at room temperature to form a material which is useful according to the present invention. One skilled in the art would also recognize that the dihydric alcohol ethylene glycol may be useful in the present invention, but may cause dermal reactions which limit its utility.

As stated above, the precursor is also comprised of at least one non-ionic unsaturated free radically polymerizable material which is soluble in the polyhydric alcohol. The total amount of polymerizable material (including any ionic monomers, if present) in the precursor will generally range from about 20 to 30, preferably about 25 to 28, parts by weight of the precursor. The type of non-ionic polymerizable material used is not critical so long as it provides the desired performance properties in the cured and crosslinked state, e.g., conformability, tackiness, cohesiveness, dermal nonirritability, etc. Examples of useful non-ionic free radically polymerizable monomers which are soluble in the polyhydric alcohol are acrylic acid, methacrylic acid, hydroxyethyl methacrylate, and N-vinyl pyrrolidone. The most preferred performance properties for ECG electrodes are provided by acrylic acid in an amount between about 25 and 28 parts by weight of the precursor.

The precursor is further comprised of 0.1 to 5 parts by weight per 100 parts of the unsaturated material of a crosslinking agent of a multifunctional unsaturated free radically polymerizable material. Examples are triethylene-glycol-bis-methacrylate, ethyleneglycol-bismethacrylate, bisacrylamide, and triethyleneglycol-bisacrylate with the former being preferred in amounts about 0.15 to about 1.5 parts by weight per 100 parts of the unsaturated material.

The initiation of polymerization of the precursor is facilitated by the presence of at least 0.1 part by weight per 100 parts of the unsaturated material of a free radical initiator which is soluble in the polyhydric alcohol. The initiator may be of the thermal or photo class. The actual selection is dependent on the monomers and the polyhydric alcohol. An example of useful thermal initiators are benzoyl peroxide, azobisisobutyronitrile, di-t-butyl peroxide and cumyl peroxide. Examples of useful photoinitiators are disclosed in the article Photoinitiators—An Overview by G. Berner et al in the Journal of Radiation Curing (April 1979), pp. 2 through 9. The preferred photoinitiator is benzildimethylketal.

The electrical conductivity of the adhesives of the invention is provided by the addition of an effective amount of an ionizable salt to the adhesive precursor. The salt is preferably present in an amount ranging from about 0.1 to 5.5 percent by weight of the precursor. Any organic or inorganic ionizable salt may be used which provides the necessary electrical conductivity, is dermally-nonirritating, does not interfere with the physical properties of the adhesive and, in the case of ECG electrodes, allows the electrode to exhibit the required Polarization Potential, i.e., recover rapidly following defibrillation overload. It has been found that ionizable salts containing halide ions provide the best overall results, especially inorganic halide salts containing chloride and bromide ions. Particularly preferred are inorganic chloride salts such as potassium chloride. The most preferred adhesive precursor contains potassium chloride in a concentration between 3.5 and 4.5 percent by weight of the precursor.

In some cases, it may be necessary to add a small amount of water, e.g., 10 percent by weight or less, to the precursor to ensure complete solubilization of the salt. The water becomes part of the conductive adhesive coating and may evaporate to some extent if the electrode is used or stored in environments of low humidity and/or high temperature. However, under normal conditions, the small water content appears to have little or no negative effect on the performance of the electrode.

It will be recognized by one skilled in the art that other additives (e.g., tackifers, such as polyacrylic acid) may be added to the precursor. In fact, the preferred precursor contains about 4.0 percent by weight of polyacrylic acid to increase tackiness.

The essentially solventless precursor can be coated on to the electrode plate or transfer sheet and, depending on the free radical initiator, exposed to either heat or actinic radiation which results in the formation of an electrically conductive pressure-sensitive adhesive. The precursor may also be exposed to electron beam radiation to facilitate the crosslinking.

DESCRIPTION OF THE DRAWINGS

A better understanding of the invention will be facilitated by reference to the accompanying drawings wherein:

FIG. 1 is an exploded sectional view of a disposable ECG electrode containing the conductive adhesive of the invention;

FIG. 2 is a top plan view of an alternative embodiment of the ECG electrode of FIG. 1;

FIG. 3 is an exploded sectional view of the electrode of FIG. 2; and

FIG. 4 is a circuit used in the defibrillation overload recovery test (described in example 1 below).

Referring to FIG. 1, a disposable ECG electrode 10 is illustrated in which the electrode plate 12 is provided by a circular piece of nonwoven web 14 approximately 1 3/16 inches in diameter which has been vapor coated with silver 16 on its lower surface. Electrode plate 12 is connected to an electrocardiograph (not shown) by means of a standard stud/eyelet connector. In the embodiment illustrated, stud 18 is made of stainless steel and eyelet 20 is formed of plastic (injection molded ABS) having a conventional silver/silver chloride coating. Conductive adhesive layer 22, approximately 28 mils thick, covers the lower, skin-directed surface of the electrode plate 12. A release liner 24 protects the conductive adhesive prior to use.

The electrode 26 of FIGS. 2 and 3 comprises a circular piece of standard pressure-sensitive adhesive tape 28 such as Micropore® brand tape sold by the 3M Company, Saint Paul, Minn. Adhesive tape 28 is laminated to a disc of tin foil 30 approximately 1.7 mils thick and 1 ¼ inches in diameter. Tin foil disc 30 constitutes the conductive electrode plate of the electrode. Tab 32 extends from tape 28 and tin foil disc 30 to provide a means for connecting the electrode plate to an electrocardiograph by way of any alligator clamp (not shown) or other suitable connector. Tab 32 is reinforced with a piece of polyethylene 34 (preferably colored) so as to be readily visible to the user. Conductive adhesive layer 36, approximately 28 mils thick, is applied to the lower, skin-directed surface of tin foil disc 30. Release liner 38 is used to protect the adhesive prior to use.

No elaborate packaging is required for electrodes according to the invention since they are essentially "dry" and moisture loss is generally not a problem.

The embodiments illustrated in the drawings are merely illustrative. The specific construction of the electrode is not critical to the invention. The ECG electrodes illustrated are designed to have a low Polarization Potential in accordance with the standards proposed by AAMI. It is well known to those skilled in the art that to achieve a low Polarization Potential the electrode plate must be selected so as to be non-polarizing. Silver-silver chloride or tin electrode plates in combination with a conductive adhesive containing chloride ion are preferably used. Other suitable materials include nobel metals, but they are not practical on account of cost.

The conductive adhesives of the present invention may be used in biomedical electrodes other than nonpolarizing ECG electrodes, such as electrosurgical grounding plate electrodes and electrodes for transcutaneous electrical nerve stimulation (TENS). However, for such other applications, they offer no perceived advantages over the conductive adhesives described in my previous disclosure, Ser. No. 114,565, filed Jan. 23, 1980. In some cases they may be less desirable, particularly since the presence of an ionizable salt in the present adhesive may cause some corrosion problems when used in combination with certain metal electrode plates such as aluminum.

The invention is further illustrated by reference to the following non-limiting examples.

EXAMPLE 1

Powdered polyacrylic acid as the sodium salt (18 grams) (K 739 from B. F. Goodrich Chemical Division, Cleveland, Ohio) is dissolved in warm distilled water (18 grams) by stirring for one hour, and added to a mixture of potassium chloride (17.1 grams), distilled water (25.0 grams), acrylic acid (115.0 grams), glycerine (250.0 grams), triethyleneglycol-bis-methacrylic (0.3 grams) and 0.35 grams of Irgacure 651 (a benzildimethylketal from Ciba-Geigy). The ingredients are mixed for 4 hours in a glass jar to insure dissolution of all components. During mixing, the jar is covered with aluminum foil to prevent premature polymerization.

This adhesive precursor is knife-coated onto 8-pound tissue paper (from Crystal Tissue Company) which is layered on 76-pound silicone coated paper (from the H. P. Smith Company). The resulting coating adhesive thickness is approximately 28 mils.

The coated substrate is then passed through a 3-foot inert chamber ($N_2$ atmosphere) under a bank of UV lights consisting of thirty 18-inch "black light" tubes for one minute which results in the polymerization of the coating.

A 4 mil web of nonwoven polyester number 760 from 3M Company, Industrial Electrical Products Division was vaporcoated with 2000° A silver. Stainless steel studs and silver/silver chloride-plated plastic eyelets were crimped through the silver vaporcoated film. This film was then hand laminated to the polymerized conductive adhesive and 1 3/16 inch diameter electrodes as illustrated in FIG. 1 were produced. These electrodes were allowed to equilibrate for one day at 50% relative humidity (R.H.) and 74° F. After equilibrating for one day the samples were tested for conductivity and defibrillator recovery.

Impedance

Impedance in ohms of the electrode was measured using a Model 4800A Vector Impedance Meter manufactured by Hewlett Packard, Palo Alto, Calif. Measurements were conducted in the conventional manner on electrode pairs connected face-to-face (adhesive-to-adhesive) using a low level signal suitable for measurements on ECG electrodes. The impedance of the electrode at 10 Hz was found to be 185 Ohms.

Polarization Potential

The Polarization Potential of the electrode was determined using the defibrillation overload recovery test set forth in "AAMI Draft Standard for Pregelled Disposable Electrodes", May, 1981, Section 2.2.2.4, Electrical Performance Standards. The test was conducted as follows using the circuit shown in FIG. 4:

1. Two electrodes 40 and 42 are connected adhesive-to-adhesive and connected to the test circuit (FIG. 3) with switch 44 closed and switches 46 and 48 open.

2. At least 10 seconds are allowed for the capacitor 50 to fully charge to 200 V; switch 44 is then opened.

3. The capacitor 50 is discharged through the electrode pair by holding switch 46 closed long enough to discharge the capacitor 50 to less than 2 V. This time should be no longer than 2 seconds.

4. Switch 48 is closed immediately, and the electrode pair is connected to the offset measurement system (switch 46 open).

5. The electrode offset is recorded to the nearest 1 mV, 5 seconds after the closure of switch 48 and every 10 seconds thereafter for the next 30 seconds. The overload and measurement is repeated three times.

The test circuit of FIG. 4 should have the following characteristics: Resistor 52 has a resistance of 10 kilohms, and resistor 54 is a 5 watt, 100 ohm resistor. Capacitor 50 has a capacitance of 10 $\mu$F. All capacitors and resistors should be within 90 to 110 percent of the specified values. The offset recorder input amplifier 56 has a resistance of 10 megohms and must have an input impedance from 0 to 10 Hz of 10 M, ±10 percent, and a bias current of less than 200 nA. The error of the voltage-recording equipment should be no greater than ±5 percent of full scale of 100 mV. A 10 mV change must be measurable with an error no greater than ±1 mV. For this purpose, the full scale range and resolution of the recording instrument may be adjusted as needed.

The test sequence (Steps 1–5) is repeated for 3 electrode pairs. The "Polarization Potential" (as used herein means the potential 15 second after the fourth pulse) should not exceed 100 millivolts. The electrode of this example was found to have a Polarization Potential of 18.8 millivolts.

Following the manufacturing and testing procedures set forth in Example 1, the following electrodes were made.

| Example No. | Salt | Amount (grams) | % | Impedence (10 Hz) | Polarization Potential |
|---|---|---|---|---|---|
| 2 | CaCl$_2$ | 8.6 | 1.97 | 500 ohms | 19.5 mv |
| 3 | KBr | 17.1 | 3.85 | 1600 | 7.2 |
| 4 | NH$_4$Cl | 8.6 | 1.97 | 770 | 18.0 |
| 5 | NaCl | 17.1 | 1.97 | 425 | 17.8 |
| 6 | SnCl$_4$ | 17.1 | 1.97 | 2900 | 15.5 |
| 7 | KCl | 0.43 | 0.10 | 850 | 91.0 |
| 8 | KCl | 23.5 | 5.22 | 240 | 14.7 |
| 9 | None | — | — | 1150 | 255.0 |

When no salt was used and 8 percent potassium hydroxide was present (according to the disclosure of Ser. No. 114,565, filed Jan. 23, 1980), the impedance was 200 ohms and the Polarization Potential was 350 millivolts. A combination of potassium hydroxide and potassium chloride, 2% and 4%, respectively, brought the impedance down to 130 ohms and the Polarization Potential to 20 millivolts.

The following examples illustrate adhesive precursors containing different nonionic monomers and an assessment of the adhesive properties (initial thumb tack) of the cured adhesive.

EXAMPLE 10

| Ingredient | Amount (grams) | Initial Thumb Tack |
|---|---|---|
| KCl | 5.7 | |
| Water distilled | 8.3 | |
| Dissolved polyacrylic acid (sodium salt) in water (50% by weight) | 12.0 | |
| Methacrylic acid | 38.3 | high tack |
| Irgacure 651 | .12 | |
| Glycerine | 83.3 | |
| TEGBM | .1 | |

EXAMPLE 11

| Ingredient | Amount (grams) | Initial Thumb Tack |
|---|---|---|
| KCl | 5.7 | |
| Water distilled | 8.3 | |
| Dissolved polyacrylic acid (sodium salt) in water (50% by weight) | 12.0 | |
| Hydroxyethyl methacrylate | 38.3 | low-medium tack |
| Irgacure 651 | .12 | |
| Glycerine | 83.3 | |
| TEGBM | .1 | |

EXAMPLE 12

| Ingredient | Amount (grams) | Initial Thumb Tack |
|---|---|---|
| KCl | 17.1 | |
| Water | 25.0 | |
| Dissolved poly acylic acid (sodium salt) in water (50% by weight) | 36.0 | |
| N—vinyl pyrrolidone | 115.0 | high tack |
| Irgacure 651 | | |
| Glycerine | 250.0 | |
| TEGBM | .3 | |

EXAMPLE 13

| Ingredient | Amount (grams) | Initial Thumb Tack |
|---|---|---|
| KCl | 5.7 | |
| Water | 8.3 | |
| Dissolved poly acylic acid (sodium salt) in water (50% by weight) | 12.0 | |
| Acrylic acid | 20.0 | high tack |
| Hydroxyethyl methacrylate | 18.3 | |
| Irgacure 651 | .12 | |
| Glycerine | 83.3 | |
| TEGBM | .1 | |

EXAMPLE 14

| Ingredient | Amount (grams) | Initial Thumb Tack |
|---|---|---|
| KCl | 17.1 | |
| Water | 25.0 | |
| Acrylic acid | 115.0 | high tack |
| Irgacure 651 | 0.35 | |
| Glycerine | 250.0 | |
| Triethylene glycol dimethacrylate | 0.3 | |

The following examples illustrate adhesive precursors containing different polyhydric alcohols and an assessment of the adhesive properties of the cured adhesive.

EXAMPLE 15

| Ingredient | Amount (grams) | Initial Thumb Tack |
|---|---|---|
| KCl | 5.7 | |
| Water | 8.3 | |
| Dissolved poly acrylic acid (sodium salt) in | 12.0 | medium tack |

-continued

| Ingredient | Amount (grams) | Initial Thumb Tack |
|---|---|---|
| water (50% by weight) | | |
| Acrylic acid | 38.3 | |
| Irgacure 651 | .12 | |
| Propylene glycol | 83.3 | |
| TEGBM | .1 | |

EXAMPLE 16

| Ingredient | Amount (grams) | Initial Thumb Tack |
|---|---|---|
| KCl | 5.7 | |
| Water | 8.3 | |
| Dissolved poly acrylic acid (sodium salt) in water (50% by weight) | 12.0 | high tack |
| Acrylic acid | 38.3 | |
| Irgacure 651 | .12 | |
| 1,2,4 Butanetriol | 83.3 | |
| TEGBM | .1 | |

EXAMPLE 17

| Ingredient | Amount (grams) | Initial Thumb Tack |
|---|---|---|
| KCl | 5.7 | |
| Water | 8.3 | |
| Dissolved poly acrylic acid (sodium salt) in water (50% by weight) | 12.0 | high tack |
| Acrylic acid | 38.3 | |
| Irgacure 651 | .12 | |
| Carbowax ® #400 polyethylene oxide | 83.3 | |
| TEGBM | .1 | |

I claim:

1. In an ECG electrode comprising an electrode plate having an upper surface and a lower skin-directed surface, means for electrically-connecting said electrode plate to the lead wire of an electrocardiograph, and a layer of an electrically-conductive pressure-sensitive adhesive on the lower surface of electrode plate, the improvement wherein said adhesive comprises a non-ionic swellable, conformable, cohesive, dermally-non-irritating hydrophilic synthetic cross-linked acrylic acid polymer; polyhydric alcohol which is liquid at about 20° C.; and an ionizable salt in an amount effective to render said adhesive electrically-conductive; said polymer being polymerized and cross-linked after formation into said layer to form a continuous covalently-bonded network throughout said layer.

2. The electrode according to claim 1 wherein said ionizable salt contains a halide ion.

3. The electrode according to claim 2 wherein said halide ion is chloride.

4. The electrode according to claim 3 wherein said salt is potassium chloride.

5. The electrode according to claim 1 wherein said polyhydric alcohol comprises from about 10 to about 90 parts per weight of said adhesive.

6. The electrode according to claim 5 wherein said polyhydric alcohol is glycerol.

7. The electrode according to claim 1 wherein said adhesive further comprises a tackifier selected from the group consisting of polyacrylic acid and soluble salts thereof.

8. The electrode according to claim 1 wherein said electrode plate comprises a layer of metal foil.

9. The electrode according to claim 8 wherein said metal is tin.

10. The electrode according to claim 1 wherein said electrode plate comprises a non-woven web having metallic silver vapor-coated on the lower surface thereof.

11. In a biomedical electrode comprising an electrode plate having an upper surface and a lower skin-directed surface, said electrode plate having means for electrical connection to a lead wire of an electro-medical device, and a layer of an electrically-conductive pressure-sensitive adhesive on said lower surface of said electrode plate for enhancing electrical connection with the skin, the improvement wherein said adhesive layer comprises a swellable, dermally-nonirritating, conformable, cohesive, hydrophilic polymer formed by the in situ photopolymerization of an adhesive precursor comprising
  (1) a water-soluble polyhydric alcohol which is a liquid at about 20° C.;
  (2) acrylic acid
  (3) a photo-initiator soluble in said polyhydric alcohol;
  (4) a crosslinking agent of a multifunctional unsaturated free radically-polymerizable material soluble in said polyhydric alcohol; and
  (5) an ionizable salt in an amount effective to render said conductive material electrically conductive;
  whereby said adhesive layer is a continuous covalently bonded network throughout said adhesive layer.

12. The essentially dry biomedical electrode according to claim 11 wherein the photo-initiator is benzildimethylketal.

* * * * *